United States Patent
Carr

(10) Patent No.: US 7,064,145 B2
(45) Date of Patent: Jun. 20, 2006

(54) INHIBITION OF BETA CELL DEGENERATION

(75) Inventor: Richard David Carr, Vaerlose (DK)

(73) Assignee: Novo Nordisk A/S, Bagsvaerd (DK)

( * ) Notice: Subject to any disclaimer, the term of this patent is extended or adjusted under 35 U.S.C. 154(b) by 4 days.

(21) Appl. No.: 09/790,002

(22) Filed: Feb. 21, 2001

(65) Prior Publication Data

US 2001/0025023 A1 Sep. 27, 2001

Related U.S. Application Data

(60) Provisional application No. 60/216,202, filed on Jul. 6, 2000, provisional application No. 60/189,613, filed on Mar. 15, 2000.

(30) Foreign Application Priority Data

| Feb. 25, 2000 | (DK) | ............................. 2000 00295 |
| Jun. 23, 2000 | (DK) | ............................. 2000 00983 |
| Jan. 22, 2001 | (DK) | ..................... PCT/DK01/00045 |

(51) Int. Cl.
*A61K 31/401* (2006.01)
(52) U.S. Cl. .................................................. 514/424
(58) Field of Classification Search ................ 514/424
See application file for complete search history.

(56) References Cited

U.S. PATENT DOCUMENTS 5,585,347 A * 12/1996 Meier et al.

FOREIGN PATENT DOCUMENTS

WO        WO 98/19998         * 5/1998

OTHER PUBLICATIONS

Shafrir et al., Annals New York Academy of Sciences, Nov. 18, 1999;892:223-46.*
Holst et al., Diabetes, vol. 47, pp. 1663-1670 (1998).

* cited by examiner

*Primary Examiner*—San-Ming Hui
(74) *Attorney, Agent, or Firm*—Rosemarie R. Wilk-Orescan; Reza Green; Richard W. Bork

(57) ABSTRACT

Methods for preventing beta cell degeneration, such as necrosis or apoptosis of beta cells in a subject, comprising administering a DPP-IV inhibitor to a subject in need thereof. The invention furthermore relates to a method for increasing the number and/or the size of beta cells. The invention also relates to a method for delaying the progression of Impaired Glucose Tolerance (IGT) to type 2 diabetes, as well as a method for delaying the progression of non-insulin demanding type 2 diabetes to insulin-demanding type 2 diabetes.

23 Claims, No Drawings

INHIBITION OF BETA CELL DEGENERATION

CROSS-REFERENCE TO RELATED APPLICATIONS

This application claims priority under 35 U.S.C. 119 of Danish application nos. PA 2000 00295 filed Feb. 25, 2000, and PA 2000 00983 filed on Jun. 23, 2000, and U.S. provisional application Nos. 60/189,613 filed Mar. 15, 2000 and 60/216,202 filed on Jul. 6, 2000. Priority is claimed under 35 U.S.C. 120 to International Patent Application PCT/DK01/0045 filed on Jan. 22, 2001 and U.S. patent application Ser. No. 09/767,354 filed on Jan. 23, 2001, the contents of which are fully incorporated herein by reference.

The present invention relates to a method for modulating, inhibiting, decreasing, or preventing beta cell degeneration, loss of beta cell function, beta cell dysfunction, and/or death of beta cells, such as necrosis or apoptosis of beta cells in a subject, comprising administering a DPP-IV inhibitor to the subject. The invention furthermore relates to a method for increasing the number and/or the size of beta cells. The invention also relates to a method for delaying the progression of Impaired Glucose Tolerance (IGT) to type 2 diabetes, as well as a method for delaying the progression of non-insulin demanding type 2 diabetes to insulin-demanding type 2 diabetes.

BACKGROUND

Diabetes is characterized by insufficiency of the pancreatic beta cells to maintain normoglycemia. In type 1 diabetes this is due to destruction of the beta cells by an autoimmune process, whereas in type 2 diabetes it is due to a combination of beta cell deficiency and peripheral insulin resistance.

What most textbooks of pathology describe as cell death is coagulative necrosis. This is an abnormal morphological appearance, detected in tissue examined under the microscope. The changes, which affect aggregates of adjacent cells or functionally related cohorts of cells, are seen in a variety of contexts produced by accident, injury, or disease. Among the environmental perturbations that may cause cell necrosis are oxygen deprivation (anoxia), hyperthermia, immunological attack, and exposure to various toxins that inhibit crucial intracellular metabolic processes. Coagulative necrosis is the classical form of cell change seen when tissues autolyze (digest themselves) in vitro.

Apoptosis is an active process of cellular self-destruction that is regulated by extrinsic and intrinsic signals occurring during normal development. It is well documented that apoptosis plays a key role in regulation of pancreatic endocrine beta cells. There is increasing evidence that in adult mammalians the beta cell mass is submitted to dynamic changes to adapt insulin production for maintaining euglycemia in particular conditions, such as pregnancy and obesity. The control of beta cell mass depends on a subtle balance between cell proliferation, growth and cell death (apoptosis). A disruption of this balance may lead to impairment of glucose homeostasis.

Apoptosis is also associated with diseases such as cancer, immunological disorders, and neurodegenerative disorders.

Published patent application WO 9310127 discloses proline boronic esters useful as DPP-IV inhibitors.

Published patent application WO 9515309 discloses amino acid 2-cyanopyrrolidine amides as inhibitors of DPP-IV.

Published patent application WO 9529691 discloses peptidyl derivates of diesters of alpha-aminoalkylphosphonic acids, particularly those with proline or related structures.

Published patent application WO 9819998 discloses N-(N'-substituted glycyl)-2-cyano pyrrolidines, in particular 1-[2-[5-Cyanopyridin-2-yl]amino]-ethylamino]acetyl-2-cyano-(S)-pyrrolidine (NVP-DPP728).

Published patent application WO 9925719 discloses sulphostin, a DPP-IV inhibitor prepared by culturing a *Streptomyces* microorganism.

Published patent application WO 9938501 discloses N-substituted 4-8 membered heterocyclic rings.

Geman utility models DE 29909208 U, DE 29909210 U, and DE 29909211 U disclose val-pyr, val-thiazolidide, isoleucyl-thiazolidide, isoleucyl-pyrrolidine, and fumar salts of isoleucyl-thiazolidide and isoleucyl-pyrrolidide.

Published patent application WO 9946272 discloses phosphoric compounds as inhibitors of DPP-IV.

Published patent applications WO 9967278 and WO 9967279 disclose DPP-IV prodrugs and inhibitors of the form A-B-C where C is either a stable or unstable inhibitor of DPP-IV.

Published patent application WO 0034241 and published U.S. Pat. No. 6,110,949 disclose N-substituted adamantyl-amino-acetyl-2-cyano pyrrolidines and N-(substituted glycyl)-4-cyano pyrrolidines respectively.

In WO 97/40832 is disclosed use of DPP-IV inhibitors for lowering the blood glucose level in mammals.

BRIEF SUMMARY OF THE INVENTION

The present invention relates to a method of treating beta cell degeneration comprising administering a DPP-IV inhibitor. "Beta cell degeneration" includes necrosis or apoptosis of β-cells. "Treatment" or "treating" beta cell degeneration includes preventing, modulating, inhibiting, and/or decreasing beta cell degeneration. The term "inhibition," and "decreasing" are meant to include reduction and arresting beta cell degeneration.

The invention also relates to use of a DPP-IV inhibitor for the preparation of a medicament for increasing the number of beta cells.

In another aspect, the invention is a method of increasing the size of beta cells by administering to a subject a DPP-IV inhibitor.

In yet another aspect, the invention is a method of increasing the number of beta cells by administering to a subject a DPP-IV inhibitor.

The invention furthermore relates to a method of delaying the progression of Impaired Glucose Tolerance (IGT) to type 2 diabetes by administering to a subject a DPP-IV inhibitor.

The invention furthermore relates to a method of delaying the progression of Impaired Impaired Fasting Glucose (IFG) to type 2 diabetes by administering to a subject a DPP-IV inhibitor.

The invention furthermore relates to a method of delaying the progression of non-insulin demanding type 2 diabetes to insulin demanding type 2 diabetes.

The subject is preferably a mammal, more preferably a human patient in need of treatment.

DETAILED DESCRIPTION OF THE INVENTION

The insulinotropic hormone Glucagon like peptide-1 (GLP-1) has been shown to stimulate glucose-induced insulin release and insulin biosynthesis and to restore glucose competence. In our efforts to identify beta cell growth factors we discovered that GLP-1 indeed could stimulate beta cell proliferation in vitro. The proliferation was measured as incorporation of the thymidine analogue 5-bromo-2-deoxyuridine (BrdU) into DNA in insulin-positive cells in pancreatic islet cells from newborn rats. GLP-1 was found to increase the number of labelled beta cells.

Dipeptidyl peptidase-IV (DPP-IV), a serine protease belonging to the group of post-proline/alanine cleaving amino-dipeptidases, specifically removes the two N-terminal amino acids from proteins having proline or alanine in position 2.

DPP-IV has been implicated in the control of glucose metabolism because its substrates include the insulinotropic hormones Glucagon like peptide-1 (GLP-1) and Gastric inhibitory peptide (GIP). GLP-1 and GIP are active only in their intact forms; removal of their two N-terminal amino acids inactivates them.

In vivo administration of synthetic inhibitors of DPP-IV prevents N-terminal degradation of GLP-1 and GIP, resulting in higher plasma concentrations of these hormones, increased insulin secretion and, therefore, improved glucose tolerance. It has now been found that inhibition of DPP-IV could stimulate beta cell proliferation in vivo.

Definitions

By the term "treatment" is understood the management and care of a patient for the purpose of combating the disease, condition, or disorder.

The term "beta cell degeneration" is intended to mean loss of beta cell function, beta cell dysfunction, and death of beta cells, such as necrosis or apoptosis of beta cells.

The term "Impaired Glucose Tolerance" (IGT) is intended to mean a condition indicated by a 2-h postload glucose (2-h PG) between 7.8 mmol/l and 11.1 mmol/l in an Oral Glucose Tolerance Test (OGTT) using a glucose load containing the equivalent of 75 g anhydrous glucose dissolved in water.

The term "Impaired Fasting Glucose" (IFG) is intended to mean a condition indicated by a Fasting Plasma Glucose (FPG) between 6.1 mmol/l and 7.0 mmol/l, where fasting is defined as no caloric intake for at least 8 hours.

The term non-insulin demanding type 2 diabetes is intended to mean a condition where the individual has insulin resistance, insulin deficiency and either a FPG of more than 7.0 mmol/l or a 2-h PG of more than 11.1 mmol/l when untreated, and where normoglycemia can be achieved without insulin injections.

The term insulin-demanding type 2 diabetes is intended to mean a condition where the individual has insulin resistance, insulin deficiency and either a FPG of more than 7.0 mmol/l or a 2-h PG of more than 11.1 mmol/l when untreated, and where normoglycemia can only be achieved with insulin injections.

The term "DPP-IV" as used herein is intended to mean Dipeptidyl peptidase IV (EC 3.4.14.5; DPP-IV), also known as CD26. DPP-IV cleaves a dipeptide from the N terminus of a polypeptide chain containing a proline or alanine residue in the penultimate position.

The term "DPP-IV inhibitor" is intended to indicate a molecule that exhibits inhibition of the enzymatic activity of DPP-IV, such as from 1-100% inhibition, in the assay as described in the section "Methods for measuring the activity of compounds which inhibit the enzymatic activity of CD26/DPP-IV" (see below under experimental).

In the present context "a DPP-IV inhibitor" is also intended to comprise active metabolites and prodrugs thereof, such as active metabolites and prodrugs of DPP-IV inhibitors. A "metabolite" is an active derivative of a DPP-IV inhibitor produced when the DPP-IV inhibitor is metabolised. A "prodrug" is a compound that is either metabolised to a DPP-IV inhibitor or is metabolised to the same metabolite(s) as a DPP-IV inhibitor.

In the present text, the designation "an analogue" is used to designate a peptide wherein one or more amino acid residues of the parent peptide have been substituted by another amino acid residue and/or wherein one or more amino acid residues of the parent peptide have been deleted and/or wherein one or more amino acid residues have been added to the parent peptide. Such addition can take place either in the peptide, at the N-terminal end or at the C-terminal end of the parent peptide, or any combination thereof.

The term "derivative" is used in the present text to designate a peptide in which one or more of the amino acid residues of the parent peptide have been chemically modified, e.g. by alkylation, acylation, ester formation or amide formation.

The term "enlarging" or "increasing" as used in one aspect of the invention in which a DPP-IV inhibitor is administered to increase the number and/or size of beta cells in a subject, means that the method of the invention may be used to increase the size of the beta cell population in a patient, and/or to increase the size of each beta cell in the subject.

The invention also relates to the use according to any of the above uses in a regimen which additionally comprises treatment with human growth hormone, a growth hormone releasing agent or a growth factor such as prolactin or placental lactogen; the use of human growth hormone, a growth hormone releasing agent or a growth factor such as prolactin or placental lactogen for the preparation of a medicament for inhibiting the beta cell degeneration, such as necrosis or apoptosis of β-cells in a subject; the use of human growth hormone, a growth hormone releasing agent or a growth factor such as prolactin or placental lactogen for the preparation of a medicament for treatment of beta cell degeneration, such as necrosis or apoptosis of β-cells in a subject.

In embodiments of the invention the DPP-IV inhibitor is selected from peptides, polypeptides, proteins, enzymes, antibodies as well as non-peptides, e.g. a small organic molecule; each of which constitutes individual embodiments.

In a still further embodiment of the invention the DPP-IV inhibitor is a non-peptide.

In a preferred embodiment, the DPP-IV inhibitor is a N-substituted adamantyl-amino-acetyl-2-cyano pyrrolidine or a N-(substituted glycyl)-4-cyano pyrrolidine.

In another embodiment of the invention the DPP-IV inhibitor exhibits inhibition of DPP-IV from 1 to 100%. Further embodiments are individually at least 10% inhibition, from 10 to 100% inhibition, or from 10 to 90% inhibition.

Any possible combination of two or more of the embodiments described herein is comprised within the scope of the present invention.

The route of administration may be any route, which effectively transports the active compound to the appropriate or desired site of action, such as oral, nasal, pulmonary, transdermal or parenteral, in particular oral.

Pharmaceutical compositions (or medicaments) containing a DPP-IV inhibitor may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition that may be a powder or a liquid for the administration of the DPP-IV inhibitor in the form of a nasal or pulmonal spray. As a still further option, the DPP-IV inhibitor can also be administered transdermally, e.g. from a patch, optionally a iontophoretic patch, or transmucosally, e.g. bucally. As a still further option, the DPP-IV inhibitor can also be administered by gene therapy, such as by implanting a cell line transformed with a vector such that it secretes the DPP-IV inhibitor. The implanted cells may be encapsulated in semi permeable membranes, e.g. macro- or microencapsulated. The above-mentioned possible ways to administer a DPP-IV inhibitor are not considered as limiting the scope of the invention.

Pharmaceutical compositions containing a DPP-IV inhibitor may be prepared by conventional techniques, e.g. as described in Remington's *Pharmaceutical Sciences*, 1985 or in Remington: *The Science and Practice of Pharmacy*, 19$^{th}$ edition, 1995.

Thus, the injectable compositions of the DPP-IV inhibitor can be prepared using the conventional techniques of the pharmaceutical industry which involves dissolving and mixing the ingredients as appropriate to give the desired end product.

Further to the above-mentioned components, solutions containing a DPP-IV inhibitor may also contain a surfactant in order to improve the solubility and/or the stability of the DPP-IV inhibitor.

A composition for nasal administration of certain peptides may, for example, be prepared as described in European Patent No. 272097 (to Novo Nordisk A/S) or in WO 93/18785.

If a solid carrier is used for oral administration, the preparation may be tabletted, placed in a hard gelatine capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

The DPP-IV inhibitor can be used in the treatment of various diseases. The particular DPP-IV inhibitor to be used and the optimal dose level for any patient will depend on the disease to be treated and on a variety of factors including the efficacy of the specific peptide derivative employed, the age, body weight, physical activity, and diet of the patient, on a possible combination with other drugs, and on the severity of the case. It is recommended that the dosage of the DPP-IV inhibitor be determined for each individual patient by those skilled in the art.

EXPERIMENTAL

EXAMPLE 1

Methods for Measuring the Activity of Compounds that Inhibit the Enzymatic Activity of CD26/DPP-IV Chemical compounds are tested for their ability to inhibit the enzyme activity of purified CD26/DPP-IV. Briefly, the activity of CD26/DPP-IV is measured in vitro by its ability to cleave the synthetic substrate Gly-Pro-p-nitroanilide (Gly-Pro-pNA). Cleavage of Gly-Pro-pNA by DPP-IV liberates the product p-nitroanilide (pNA), whose rate of appearance is directly proportional to the enzyme activity. Inhibition of the enzyme activity by specific enzyme inhibitors slows down the generation of pNA. Stronger interaction between an inhibitor and the enzyme results in a slower rate of generation of pNA. Thus, the degree of inhibition of the rate of accumulation of pNA is a direct measure of the strength of enzyme inhibition. The accumulation of pNA is measured spectrophotometrically. The inhibition constant, Ki, for each compound is determined by incubating fixed amounts of enzyme with several different concentrations of inhibitor and substrate.

Materials:

The following reagents and cells are commercially available: Porcine CD26/DPP-IV (Sigma D-7052), Gly-Pro-pNA (Sigma G0513).

Assay buffer: 50 mM Tris pH7.4, 150 mM NaCl, 0,1% Triton X-100.

Gly-Pro-pNA Cleavage-Assay for CD26:

The activity of purified CD26/DPP-IV is assayed in reactions containing: 70 μl assay buffer, 10 μl inhibitor or buffer, 10 μl substrate (Gly-Pro-pNA from a 0.1 M stock solution in water) or buffer, 10 μl enzyme or buffer Reactions containing identical amounts of enzyme, but varying concentrations of inhibitor and substrate, or buffer as control, are set up in parallel in individual wells of a 96-well ELISA plate. The plate is incubated at 25° C. and absorbance is read at 405 nm after 60 min incubation. The inhibitor constants are calculated by nonlinear regression hyperbolic fit and the result is expressed as inhibition constant (Ki) in nM.

Methods for Detection of Apoptosis:

Apoptosis and inhibition thereof can be detected in the following way: The free 3' OH strand breaks resulting from DNA degradation which is associated with apoptosis can be detected with the terminal deoxynucleotidyl transferase-mediated dUTP-X3' nick end-labeling (TUNEL) technique (J Cell Biol 199: 493, 1992) or using the following kits e.g. In Situ Cell Death Detection kit; Boehringer Mannheim, Mannheim or ApoTag, Oncor, Gaithersburg, Md.). Preparation of pancreatic sections or islet cultures for apoptosis staining using the TUNEL technique is described in (Diabetologia 42: 566, 1999 and Diabetes 48: 738, 1999).

Apoptosis can also be detected by electrophoresis of the soluble DNA fraction isolated from cultured islets by quantifying the ladder-like appearance as described in (PNAS 95: 2498, 1998).

Finally apoptosis can be detected by double staining of cultured beta cellslislets with the DNA binding dyes Hoechst 33342 and propidium iodide as described in (Diabetologia 42: 55, 1999 and J. Clin. Invest. 98(7):1568–1574, 1996).

EXAMPLE 2

Effect of Administration of DPP-IV Inhibitor on Pancreatic Tissue Regeneration and Insulin Production A 60% pancreatectomy was performed on a total of 12 male Sprague-Dawley rats. Vehicle and the DPP-IV inhibitor Val-Pyr was administered to 6 of these from day 4 to 8 in a dose of 20 mg/kg p.o. x2, while the remaining 6 rats were treated with vehicle alone.

The proliferation of beta cells was measured as incorporation of the thymidine analogue 5-bromo-2-deoxyuridine (BrdU) into DNA in insulin-positive cells. 8 days after the 60% pancreatectomy, 100 mg/kg BrdU was administered i.p. and 4 hours later the area containing remnant and regenerated pancreatic tissue was removed and processed for immunohistochemistry. Three adjacent sections from each animal were stained for insulin and BrdU. The qualitative evaluation of these sections is summarised in Table 1. The amount of regenerated tissue was scored on the following range: –, (+), +, ++, +++. The location of BrDU was examined in regenerated pancreatic (reg) and exocrine (ex) tissue. Insulin staining was scored as weak (W), normal (N), and in regenerated tissue (+R).

In 5 out of 6 animals treated with Val-Pyr, insulin was expressed in islets located in the regenerating pancreatic tissue. This was only the case for 1 out of 6 animals treated with vehicle alone. These results indicate that val-pyr accelerates the differentiation process in the regenerating tissue, leading to faster formation of new beta cells. This result is in good agreement with the significant decrease of the glucose excursion (AUC reduced to app. 50% of vehicle) seen in the same val-pyr treated animals after an Oral Glucose Tolerance Test (OGTT) at day 8.

In virtually all animals from the groups treated with Val-Pyr or vehicle a strong nuclear immunostaining signal for BrdU is found in single cells dispersed in the remnant exocrine tissue and in the regenerated tissue. In certain foci of exocrine tissue often located immediately adjacent to the regenerating tissue the BrdU positive exocrine cells are densely packed. Compared with these foci, the number of BrdU positive cells in the regenerating tissue is much lower and in some cases almost no BrdU positive cells are seen in the regenerating tissue.

TABLE 1

Qualitative evaluation of remnant and regenerated pancreatic tissue stained for insulin and 5-Bromo-2-Deoxyuridine (BrdU).

| Treatment | Amount of regenerated tissue | BrDU (+/−) | Insulin |
|---|---|---|---|
| Val-Pyr 20 mg/kg | + | ++Ex +reg | W +R |
| | + | ++Ex | W +R |
| | + | +Ex | W |
| | + (inside liver) | +Ex | W +R |
| | ++ | +Ex +reg | W +R |
| | + | − | W (+R) |
| Vehicle (2 ml/kg) | (+) | +Ex | W |
| | (+) | − | W |
| | ++ | +Ex +reg | W +R |
| | (+) | +Ex | W |
| | (+) | +Ex | W |
| | + | +Ex +reg | W |

The invention claimed is:

1. A method of inhibiting beta cell degeneration in a subject suffering from loss of beta cell function, beta cell dysfunction, necrosis or apoptosis of beta cells, said method comprising administering a DPP-IV inhibitor to said subject, wherein the DPP-IV inhibitor is selected from N-substituted adamantyl-amino-acetyl-2-cyano pyrrolidine or N-(substituted glycyl)-4-cyano pyrrolidine.

2. The method of claim 1 wherein beta cell degeneration is necrosis of beta cells.

3. The method of claim 1 wherein beta cell degeneration is apoptosis of beta cells.

4. The method of claim 1, wherein the DPP-IV inhibitor is 1-[[[2-[(5-cyanopyridin-2-yl)amino]-ethyl]amino]acetyl]-2-cyano-(S)-pyrrolidine.

5. The method of claim 1, said further comprising administering to said subject one or more of human growth hormone or a growth factor.

6. The method of claim 5, wherein the growth factor is one of prolactin or placental lactogen.

7. The method of claim 1, wherein the subject is a human.

8. A method of increasing beta cell population size in a subject suffering from a decrease in the number of beta cells in its beta cell population, said method comprising administering a DPP-IV inhibitor to said subject, wherein the DPP-IV inhibitor is selected from N-substituted adamantyl-amino-acetyl-2-cyano pyrrolidine or N-(substituted glycyl)-4-cyano pyrrolidine.

9. A method of increasing individual beta cell size in a subject suffering from a decrease in individual beta cells size, said method comprising administering a DPP-IV inhibitor to said subject, wherein the DPP-IV inhibitor is selected from N-substituted adamantyl-amino-acetyl-2-cyano pyrrolidine or N-(substituted glycyl)-4-cyano pyrrolidine.

10. A method of delaying the progression of Impaired Glucose Tolerance to type 2 diabetes in a subject suffering from Impaired Glucose Tolerance in need of such treatment, said method comprising administering a DPP-IV inhibitor to said subject, wherein the DPP-IV inhibitor is selected from N-substituted adamantyl-amino-acetyl-2-cyano pyrrolidine or N-(substituted glycyl)-4-cyano pyrrolidine.

11. A method of delaying the progression of Impaired Fasting Glucose to type 2 diabetes in a subject suffering from impaired Fasting Glucose in need of such treatment, said method comprising administering a DPP-IV inhibitor to said subject, wherein the DPP-IV inhibitor is selected from N-substituted adamantyl-amino-acetyl-2-cyano pyrrolidine or N-(substituted glycyl)-4-cyano pyrrolidine.

12. A method for delaying the progression of non-insulin demanding type 2 diabetes to insulin-demanding type 2 diabetes in a subject suffering from non-insulin demanding type 2 diabetes in need of such treatment, said method comprising administering a DPP-IV inhibitor to said subject, wherein the DPP-IV inhibitor is selected from N-substituted adamantyl-amino-acetyl-2-cyano pyrrolidine or N-(substituted glycyl)-4-cyano pyrrolidine.

13. The method of claim 1, wherein the DPP-IV inhibitor is administered orally to said subject.

14. The method of claim 8, wherein the DPP-IV inhibitor is administered orally to said subject.

15. The method of claim 9, wherein the DPP-IV inhibitor is administered orally to said subject.

16. The method of claim 10, wherein the DPP-IV inhibitor is administered orally to said subject.

17. The method of claim 11, wherein the DPP-IV inhibitor is administered orally to said subject.

18. The method of claim 12, wherein the DPP-IV inhibitor is administered orally to said subject.

19. The method of claim 8, wherein the DPP-IV inhibitor is 1-[[[2-[(5-cyanopyridin-2-yl)amino]-ethyl]amino]acetyl]-2-cyano-(S)-pyrrolidine.

20. The method of claim 9, wherein the DPP-IV inhibitor is 1-[[[2-[(5-cyanopyridin-2-yl)amino]-ethyl]amino]acetyl]-2-cyano-(S)-pyrrolidine.

21. The method of claim 10, wherein the DPP-IV inhibitor is 1-[[[2-[(5-cyanopyridin-2-yl)amino]-ethyl]amino]acetyl]-2-cyano-(S)-pyrrolidine.

22. The method of claim 11, wherein the DPP-IV inhibitor is 1-[[[2-[(5-cyanopyridin-2-yl)amino]-ethyl]amino]acetyl]-2-cyano-(S)-pyrrolidine.

23. The method of claim 12, wherein the DPP-IV inhibitor is 1-[[[2-[(5-cyanopyridin-2-yl)amino]-ethyl]amino]acetyl]-2-cyano-(S)-pyrrolidine.

* * * * *